United States Patent [19]
Kawasaki et al.

[11] Patent Number: 5,056,368
[45] Date of Patent: Oct. 15, 1991

[54] ULTRASONIC TESTING METHOD

[75] Inventors: Keiji Kawasaki, Nagoya; Koji Fushimi, Gifu, both of Japan

[73] Assignee: NGK Insulators, Ltd., Nagoya, Japan

[21] Appl. No.: 572,272

[22] Filed: Aug. 24, 1990

[30] Foreign Application Priority Data

Aug. 30, 1989 [JP] Japan .................... 1-223940

[51] Int. Cl.$^5$ ............................. G01N 9/24
[52] U.S. Cl. ........................ 73/642; 73/593; 73/622
[58] Field of Search ............. 73/593, 622, 642, 644, 73/627, 629, 637, 638, 620

[56] References Cited

U.S. PATENT DOCUMENTS

| 4,297,886 | 11/1981 | Anikeev et al. | 73/644 |
| 4,387,596 | 6/1983 | Fenkner et al. | 73/640 |
| 4,406,167 | 9/1983 | Maeda | 73/622 |
| 5,001,674 | 3/1991 | Kawasaki | 73/642 |
| 5,005,417 | 4/1991 | Kawasaki et al. | 73/593 |

FOREIGN PATENT DOCUMENTS 2719119 1/1978 Fed. Rep. of Germany .
3810906 11/1988 Fed. Rep. of Germany .
0468009 3/1969 Switzerland .

Primary Examiner—Hezron E. Williams
Assistant Examiner—Louis M. Arana
Attorney, Agent, or Firm—Armstrong, Nikaido, Marmelstein, Kubovcik & Murray

[57] ABSTRACT

An ultrasonic testing method for detection of flaws in a material to be tested having a curved surface portion by use of an ultrasonic probe, wherein a center axis of curvature of the curved surface portion of the material to be tested and the center axis of the probe are set in an eccentric relationship so that the angle of refraction of an ultrasonic wave is 90°, and the probe comprises a tip portion having a curved surface of the same kind as the curved surface portion of the material to be tested and a radius of curvature of from 1.0 to 3.0 times the radius of curvature of the curved surface portion of the material to be tested. The method enables detection of internal flaws in, particularly, a spherical or cylindrical body formed of a ceramic and used as a bearing member.

6 Claims, 2 Drawing Sheets

ULTRASONIC TESTING METHOD

BACKGROUND OF THE INVENTION AND RELATED ART STATEMENT

This invention relates to an ultrasonic testing method for detection of flaws in component parts having a curved surface portion with a specified radius of curvature, and more particularly to an ultrasonic testing method wherein a center axis of curvature of the curved surface portion of the component part and the center axis of a probe are set in an eccentric relationship.

As a testing method for detection of flaws in steel materials, steel plates, forgings, etc., there has conventionally been used an immersion type ultrasonic testing method.

The conventional immersion type ultrasonic testing is generally used where the material to be tested is comparatively large and the flaws to be detected are as large or larger than several millimeters. Therefore, the testing system used for the conventional ultrasonic testing is not a special one. Also, the probe used for transmission and reception of an ultrasonic wave in the testing is an ordinary one, namely, an immersion type probe which has a simple planar oscillator having a large diameter.

Additionally, some products to be used under such severe conditions are such that even minute flaws, if any, would cause problems in practical use of the products. Therefore, a system for ultrasonic detection of even minute flaws ranging down to several hundreds of micrometers in size has been adopted, in order to enhance reliability of flaw detection.

In the ultrasonic testing method for detecting minute flaws, a focus-type probe in which a concave resin lens is attached to the above-mentioned planar oscillator or in which the oscillator itself is shaped to be concave has been used.

In addition, studies have been made in recent years on the use of ceramics for bearing members and the like, which are required to have particularly high reliability.

Because ceramics are brittle materials, a testing method with high resolution has been desired for detection of flaws in the ceramic products. In the relatively new art of ultrasonic testing for detection of flaws in ceramics and the like, therefore, attempts have been made to enhance the sensitivity and accuracy of flaw detection by elevating the test frequency from the previous value of about 0.5-10 MHz to higher values of 15-100 MHz or by using a computer to perform image processing, and other methods.

In application of the above-mentioned prior art, however, the materials to be tested has been limited to comparatively large products of simple shapes, such as a flat plate, circular cylinder, prism, circular tube, etc. Also, the flaws, which are typically detected have been limited to those flaws being not smaller than 0.5 mm, at best, and located at a depth of several millimeters or more from the surface of the material under test. Accordingly, an attempt to detect the flaws in the surface and the sub-surface of a product having a radius of curvature of 10 mm or less, such as a bearing ball, by the prior art has failed because of scattering and reflection of the transmitted ultrasonic wave at the surface of the product and because of complicated refraction of the propagated ultrasonic wave.

An ultrasonic testing method for detection of minute flaws in the surface, and within a depth of 2 mm from the surface, of bearing rolling elements in the form of balls, cylinders or the like has been proposed in Japanese Laid-Open Patent Application (KOKAI) No. 63-243751 (1988) corresponding to U.S. Ser. No. 07/172,244 now abandoned. In this method, a focus-type probe and the rolling element as the material to be tested are disposed with a predetermined amount of eccentricity therebetween, and ultrasonic flaw detection is carried out to detect minute flaws in the surface and the sub-surface of the material. The method, however, is not applicable to materials to be tested which have a radius of curvature of not more than 10 mm or which have a special curved surface.

SUMMARY OF THE INVENTION

It is an object of this invention to provide a ultrasonic testing method which enables detection of internal flaws, including minute flaws in the surface and the sub-surface, of a material to be tested having a curved surface with a radius of curvature ranging from several tens of millimeters down to 10 mm or below. such as ceramic balls for bearings and ceramic parts for engines, gas turbines, etc., which have recently been developed.

According to this invention, there is provided an ultrasonic testing method for detection of flaws in a material to be tested having a curved surface portion by use of an ultrasonic probe, wherein a center axis of curvature of the curved surface portion and the center axis of the probe are set in an eccentric relationship so that the angle of refraction of an ultrasonic wave is 90°, and the probe comprises a tip portion having a curved surface of the same kind as the curved surface portion and a radius of curvature of from 1.0 to 3.0 times the radius of curvature of the curved surface portion.

In the method according to this invention, a probe conforming to the curved surface of the material to be tested is used. For instance, when the material to be tested has a spherical surface, a probe in which a tip portion thereof, namely, an acoustic lens or an oscillator, opposed to the material to be tested having a spherical surface is used. When the material to be tested has a cylindrical surface, a probe in which a tip portion thereof, namely, an acoustic lens or an oscillator, having a cylindrical surface is used. By use of such a probe in the ultrasonic testing method according to this invention, it is possible to make an ultrasonic wave be incident on the searching surface in a concentrated manner, and to detect flaws in the material to be tested which has a curved surface with a radius of curvature of not more than several tens of millimeters, for instance, a spherical or cylindrical body having a radius of curvature of not more than 20–3 mm.

DETAILED DESCRIPTION OF THE PREFERRED EMBODIMENTS

The probe used in this invention will now be described below while referring to FIG. 1 to 4.

FIG. 1 to 4 are each a conceptual view, in section, for illustrating the relationship between the probe used in this invention and the material to be tested which has a curved surface portion. The expression "the tip portion of the probe" used herein means an oscillator or an acoustic lens, as previously mentioned.

Figure 1:
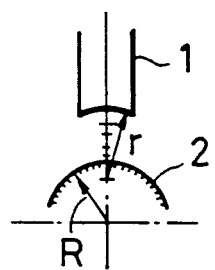
FIG. 1 is a sectional view illustrating the relationship between a probe used in this invention and the material to be tested which has a curved surface portion.

Referring to FIG. 1, the tip portion of the probe 1 which is opposed to a material to be tested 2 is shaped to have a curved surface of the same kind as the curved surface of the material to be tested, for instance, a spherical surface. The radius of curvature r of the curved surface of the tip portion is set to be from 1.0 to 3.0 times, preferably from 1.5 to 2.5 times, the radius of curvature R of the material to be tested 2. If the radius of curvature r of the tip portion is less than 1.0 times the radius of curvature R of the material to be tested, the ultrasonic wave is highly scattered in the sub-surface of the material to be tested, and noise echo is increased, resulting in poorer performance of flaw detection. If the radius of curvature of the tip portion exceeds 3.0 times the radius of curvature of the material to be tested, on the other hand, convergence of the ultrasonic wave is worsened, and a high sound pressure is not obtained, so that the performance of flaw detection is similarly poor.

Figure 2:
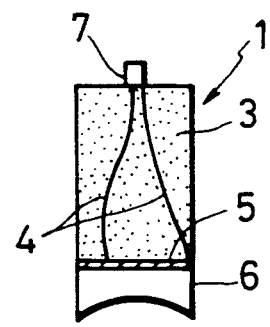
FIG. 2 and 3 are each an illustrative sectional view of a probe according to one embodiment of this invention.
Figure 3:
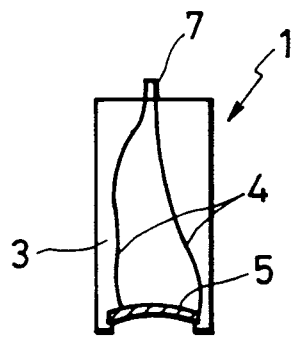

Furthermore, as shown in FIG. 2 or FIG. 3, the probe 1 used in this invention has an oscillator 5 connected to lead wires 4 extended from a connector 7 for connection to an ultrasonic transmitter-receiver through a damper 3. Thus, the tip portion of the probe which is opposed to the material to be tested is an acoustic lens 6 making intimate contact with the oscillator 5, or is the oscillator 5 itself. In this invention, the acoustic lens 6 or the oscillator 5 can be used for the probe, after being provided with a curved surface the kind of which and the radius of curvature of which are set in accordance with those of the curved surface of the material to be tested 2.

In the ultrasonic testing method of this invention, testing is conducted by setting an eccentricity between a center axis of curvature of the curved surface portion of the material to be tested and the center axis of the probe, and with such an adjustment that the angle of refraction of the ultrasonic wave will be 90°.

Figure 4:
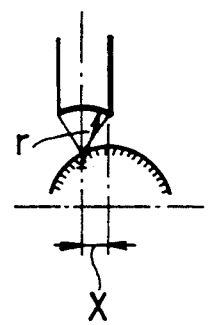
FIG. 4 is a sectional view illustrating the relationship between the focus of the probe according to this invention and the material to be tested which has a curved surface portion.

The eccentricity quantity can be calculated from, for example, the following formula (1):

$$X = R \cdot V_L / V_B \quad (1)$$

where, as shown in FIG. 4, X is the eccentricity quantity of the center axis of the probe 1, $V_L$ (m/sec) is the velocity of ultrasonic longitudinal wave in the liquid (e.g., water) in which the ultrasonic testing device is placed, and $V_B$ (m/sec) is the velocity of ultrasonic longitudinal wave in the material to be tested (e.g., ceramic ball) 2.

The method according to this invention is an ultrasonic testing method constituted as described above, by which it is possible to detect, with good accuracy, even minute flaws in a structural member or part, formed of a ceramic or the like, having a curved surface portion, particularly, a curved surface with a radius of curvature of not more than 10 mm.

Some embodiments of this invention will now be described in detail below while referring to the drawings; it is to be understood, however, that the invention is not limited to the following embodiments.

EXAMPLE 1

Figure 5:
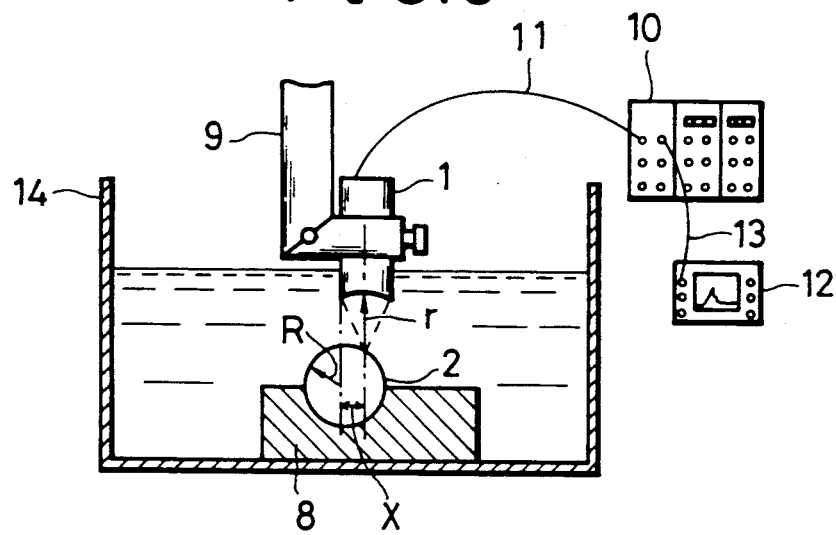
FIG. 5 is a sectional view illustrating one embodiment of a ultrasonic testing method of this invention.

FIG. 5 is a sectional view illustrating one embodiment of an ultrasonic testing method according to this invention.

Eight kinds of silicon nitride ceramic balls 10 or 20 mm in diameter were prepared which were provided therein with pores respectively 50, 100, 300 and 500 μm in diameter, by mixing resin particles into the raw material for the balls. Referring to FIG. 5, the ceramic ball 2 was first set on a ball holder 8 disposed in a water tank 14 and designed to enable free manual rotation of the ball. A probe 1 which had a test frequency of 50 MHz and in which an oscillator surface at a tip portion of the probe was a concave spherical surface with a radius of curvature of 7.5 mm was set on a probe holder 9. An eccentricity was set between the ceramic ball 2 and the center axis of the probe so that the angle of refraction of an ultrasonic wave would be 90°, the eccentricity being 1.3 mm for the balls 10 mm in diameter and being 2.6 mm for the balls 20 mm in diameter. Further, the probe holder 9 was adjusted so that the spacing between the oscillator of the probe and the surface of the ceramic ball was 7.5 mm, the value being equal to the radius of curvature of the probe. The probe 1 was connected through a high-frequency cable 11 to an ultrasonic transmitter-receiver 10 disposed in the exterior of the water tank. For observation of an ultrasonic echo reflected from the ceramic ball, an oscilloscope 12 was connected to the ultrasonic transmitter-receiver 10 by a high-frequency cable 13. In this condition, the echo was observed on the oscilloscope 12 while the ceramic ball 2 was manually rotated. After observation of the echo for the entire surface of the ceramic ball 2, the ball 2 was replaced, and this procedure was repeated until all the ceramic balls were tested. For the balls 10 mm in diameter, it was possible to detect all the flaws. However, for the balls 20 mm in diameter, only the flaws which were 500 μm in diameter were detectable.

Next, the probe was replaced by a probe which had a test frequency of 50 MHz and in which the oscillator surface was a concave spherical surface with a radius of curvature of 15 mm, and the same experiment as above was carried out. For the balls 20 mm in diameter, it was possible to detect all the flaws. However, for the balls 10 mm in diameter, it was impossible to detect the flaws 50 μm in diameter. The results of the above experiments are shown in Table 1.

COMPARATIVE EXAMPLE 1

Experiments were carried out in the same manner as in Example 1 except that the probe was replaced by a probe having a test frequency of 50 MHz and comprising a planar oscillator with an oscillator diameter of 5 mm. For both the balls 10 mm in diameter and the balls 20 mm in diameter, it was impossible to detect any flaws. The results are shown in Table 1.

TABLE 1

| | Tip portion of oscillator | | Ceramic ball radius R (mm) | r/R | Size of flaws detected (μm) |
|---|---|---|---|---|---|
| | Kind of curved surface | Radius of curvature r (mm) | | | |
| Example 1 | Concave spherical | 7.5 | 5 | 1.5 | All sizes |
| | | | 10 | 0.75 | φ 500 only |
| | Concave spherical | 15 | 5 | 3.0 | ≧ φ 100 |
| | | | 10 | 1.5 | All sizes |
| Comparative Example 1 | Planar | — | 5 | — | None |
| | | | 10 | — | None |

EXAMPLE 2

Figure 6A:
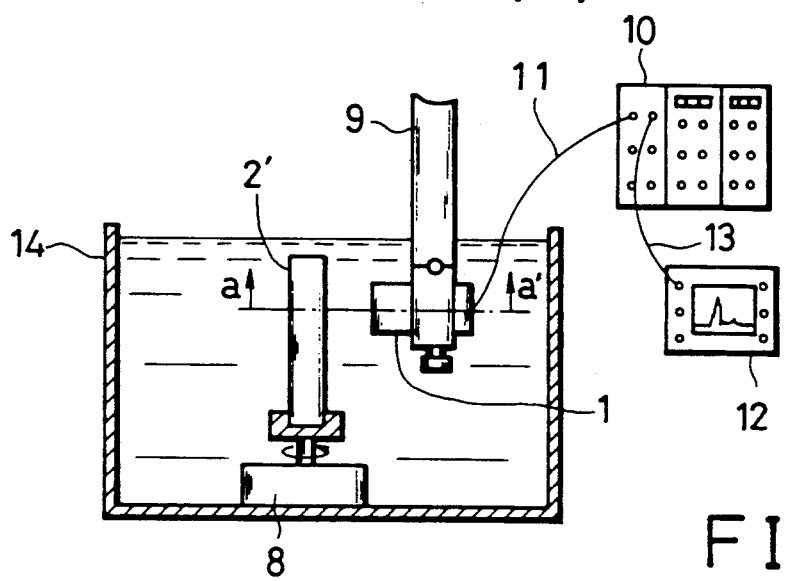
FIG. 6A is a sectional view illustrating another embodiment of the ultrasonic testing method of this invention.
Figure 6B:
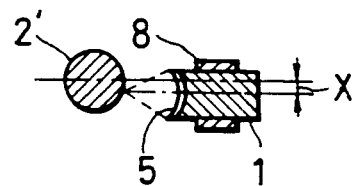
FIG. 6B is a cross-sectional view, taken along line a—a' of FIG. 6A, for illustrating the positional relationship between a cylindrical test piece and a probe.

FIG. 6A is a sectional view illustrating another embodiment of an ultrasonic testing method of this invention, and FIG. 6B is a cross-sectional view, taken along line a—a' of FIG. 6A, for illustrating the positional relationship between a cylindrical test piece and a probe.

Three cylindrical test pieces of silicon nitride having a length of 50 mm and respective diameters of 6, 10 and 20 mm were prepared which were provided therein with artificial pores (as flaws) by placing resin particles respectively 50, 100, 300 and 500 μm in diameter in the raw material for the test pieces at the time of molding. Referring to FIG. 6A, the cylindrical test piece 2' was first set on a holder 8 disposed in a water tank 14 and capable of being freely rotated horizontally. The holder 8 is so adjusted that the eccentricity of the cylindrical test piece 2' with respect to rotation would be not more than 0.1 mm. Next, a probe 1 which had a test frequency of 50 MHz and in which the oscillator surface at a tip portion of the probe is a recessed cylindrical surface with a radius of curvature of 15 mm was set on a probe holder 9. The probe holder 9 was so adjusted that, as shown in FIG. 6B, the direction of the curved surface of an oscillator surface 5 of the probe 1 coincided with the direction of the cylindrical surface of the cylindrical test piece 2', an eccentricity of 1.3 mm was set between the center axis of the cylindrical surface and the center axis of the oscillator of the probe was 1.3 mm so that the angle of refraction of an ultrasonic wave would be 90°, and the spacing between the oscillator surface and the cylindrical surface of the test piece was 15 mm, the value being equal to the radius of curvature of the oscillator surface. The probe 1 was connected through a high-frequency cable 11 to an ultrasonic transmitter-receiver 10 disposed in the exterior of the water tank. For observation of an ultrasonic echo reflected from the cylindrical test piece 2', an oscilloscope 12 was connected to the ultrasonic transmitter-receiver 10 by a high-frequency cable 13. In this condition, the echo was observed on the oscilloscope 12 while the cylindrical test piece 2' was rotated manually. After observation of the echo for the entire surface of the cylindrical test piece 2', the test piece was replaced, and this procedure was repeated to test the three cylindrical test pieces. In the case of the test piece with 6 mm diameter, it was only possible to detect the flaws which were 500 μm in diameter. On the other hand, in the case of the test piece with 10 mm diameter, it was possible to detect the flaws which were 100 μm or more in diameter, and in the case of the test piece with 20 mm diameter, it was possible to detect all the flaws.

Next, the probe was replaced by a probe having a test frequency of 50 MHz, an oscillator diameter of 5 mm and an oscillator surface being a recessed cylindrical surface with a radius of curvature of 7.5 mm, the spacing between the oscillator surface and the surface of the cylindrical test piece 2' was adjusted to 7.5 mm, and the same experiments as above were carried out. For the test pieces respectively 6 mm and 10 mm in diameter, it was possible to detect all the flaws. For the test piece with 20 mm diameter, on the other hand, it was only possible to detect the flaws not less than 300 μm in diameter.

Furthermore, the probe was replaced by a probe having a test frequency of 50 MHz, an oscillator diameter of 5 mm and an oscillator surface being a recessed spherical surface with a radius of curvature of 10 mm, and the same experiments as above were carried out. For the test piece with 20 mm diameter, it was possible to detect the flaws 500 μm in diameter. In the cases of the test pieces with respective diameters of 6 and 10 mm, it was impossible to detect any flaw. The results are shown in Table 2.

COMPARATIVE EXAMPLE 2

Experiments were carried out in the same manner as in Example 2 except that the probe was replaced by a probe having a test frequency of 50 MHz and comprising a planar oscillator with an oscillator diameter of 5 mm. In all the cases of the test pieces with respective diameters of 6, 10 and 20 mm, it was impossible to detect any flaws. The results are shown in Table 2.

TABLE 2

| | Tip portion of oscillator | | Cylindrical test piece radius R (mm) | r/R | Size of flaws detected (μm) |
|---|---|---|---|---|---|
| | Kind of curved surface | Radius of curvature r (mm) | | | |
| Example 2 | Concave cylindrical | 15 | 3 | 5.0 | φ 500 only |
| | | | 5 | 3.0 | ≧ φ 100 |
| | | | 10 | 1.5 | All sizes |
| | Concave cylindrical | 7.5 | 3 | 2.5 | All sizes |
| | | | 5 | 1.5 | All sizes |
| | | | 10 | 0.75 | ≧ φ 300 |
| Comparative Example 2 | Concave spherical | 10 | 3 | 3.3 | None |
| | | | 5 | 2.0 | None |
| | | | 10 | 1.0 | None |
| | Planar | — | 3 | — | None |
| | | | 5 | — | None |
| | | | 10 | — | None |

As can clearly be seen from the results of the above examples and comparative examples, when ultrasonic testing is carried out by using a probe comprising a tip portion having a curved surface of the same kind as a curved surface portion of the material to be tested and a radius of curvature of from 1.0 to 3.0 times, preferably from 1.5 to 2.5 times, the radius of curvature of the curved surface portion and by setting an eccentricity between the center axis of curvature of the curved surface portion of the material to be tested and the center axis of the probe so that the angle of refraction of an ultrasonic wave is 90°, it is possible to detect minute flaws in the material to be tested which has a curved surface with a diameter ranging from several tens of millimeters down to 10 mm or below.

What is claimed is:

1. An ultrasonic flaws detecting method for a material having a curved portion which comprises detecting and testing flaws of the material by using an ultrasonic probe with a tip portion having a curved surface of the same kind as the curved portion of a material and a curvature radius of from 1.0 to 3.0 times a radius of the curved portion of the material, eccentricaly setting the center axis of curvature of the curved portion and the center axis of curvature of the probe to make a refraction angle of an ultrasonic wave 90°.

2. An ultrasonic flaws detecting method according to claim 1, wherein the curved portion has a radius of curvature of not more than 20 mm.

3. An ultrasonic flaws detecting method according to claim 1 or 2, wherein the material to be tested is a spherical body or a cylindrical body.

4. An ultrasonic flaws detecting method according to claim 3, wherein the material to be tested is formed of a ceramic.

5. An ultrasonic flaws detecting method according to claim 1 or 2, wherein the curvature radius of the tip portion of the probe is from 1.5 to 2.5 times the radius of curvature of the curved portion.

6. An ultrasonic flaws detecting method according to claim 1 or 2, wherein the tip portion of the probe is an acoustic lens or an oscillator.

* * * * *